(12) United States Patent
Sühling et al.

(10) Patent No.: US 8,259,108 B2
(45) Date of Patent: Sep. 4, 2012

(54) METHOD AND APPARATUS FOR VISUALIZING AN IMAGE DATA RECORD OF AN ORGAN ENCLOSING A CAVITY, IN PARTICULAR A CT IMAGE DATA RECORD OF A COLON

(75) Inventors: Michael Sühling, Erlangen (DE); Fernando Vega-Higuera, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 750 days.

(21) Appl. No.: 12/382,957

(22) Filed: Mar. 27, 2009

(65) Prior Publication Data
US 2009/0244060 A1 Oct. 1, 2009

(30) Foreign Application Priority Data
Apr. 1, 2008 (DE) .......................... 10 2008 016 655

(51) Int. Cl.
*G06T 15/00* (2011.01)
(52) U.S. Cl. ........ 345/424; 345/419; 345/420; 345/620; 382/128; 382/154; 600/103; 600/407; 600/431; 600/443
(58) Field of Classification Search .................. 345/419, 345/421, 424, 620; 382/128, 154; 600/103, 600/407, 431, 443
See application file for complete search history.

(56) References Cited

U.S. PATENT DOCUMENTS

| | | | |
|---|---|---|---|
| 5,566,282 A | 10/1996 | Zuiderveld | |
| 6,331,116 B1 | 12/2001 | Chen et al. | |
| 6,947,784 B2 | 9/2005 | Zalis | |
| 6,996,205 B2 | 2/2006 | Capolunghi et al. | |
| 7,839,402 B2 * | 11/2010 | Dekel et al. | 345/421 |
| 8,009,167 B2 * | 8/2011 | Dekel et al. | 345/420 |
| 2008/0055308 A1 | 3/2008 | Dekel et al. | |

OTHER PUBLICATIONS

Bartroli, Anna V et al.., "Virtual Colon Unfolding", Proceedings of IEEE Visualization, Oct. 2001, pp. 411-419, U.S.
Salama, Christoph R. et al., "Opacity Peeling for Direct Volume Rendering", Eurographics, 2006, vol. 25, No. 3.
Parker, Steven et al., "Interactive Ray Tracing for Volume Visualization", IEEE Transactions on Computer Graphics and Visualization, 2005, pp. 1-13 and Bibliography, ACM Digital Library.
A German Office Action dated Apr. 10, 2008.

* cited by examiner

*Primary Examiner* — Phu K Nguyen
(74) *Attorney, Agent, or Firm* — Harness, Dickey & Pierce, P.L.C.

(57) ABSTRACT

A visualization of an image data record of an organ enclosing a cavity, in particular a CT image data record of a colon, that is reliable and has a low level of computational complexity, is performed according to a method. In at least one embodiment of the method a virtual viewer position outside the organ tissue is defined; an interface between the organ tissue and the cavity is defined with the aid of the image data record; from the middle of the cavity local gradients, that specify the rise in the absorption behavior between a gas contained in the cavity and the organ tissue, are determined; starting from the viewer position, a search beam is defined and an angle between the search beam and the gradients is determined; and a transparency value is allocated to the organ tissue as a function of the angle during visualization.

20 Claims, 3 Drawing Sheets

METHOD AND APPARATUS FOR VISUALIZING AN IMAGE DATA RECORD OF AN ORGAN ENCLOSING A CAVITY, IN PARTICULAR A CT IMAGE DATA RECORD OF A COLON

PRIORITY STATEMENT

The present application hereby claims priority under 35 U.S.C. §119 on German patent application number DE 10 2008 016 655.3 filed Apr. 1, 2008, the entire contents of which is hereby incorporated herein by reference.

FIELD

At least one embodiment of the invention relates to a method and/or an apparatus for visualizing an image data record of an organ enclosing a cavity, in particular a CT image data record of a colon.

BACKGROUND

The early detection of colon cancer is frequently very difficult, since the colorectal cancers or colon tumors very seldom cause symptoms. The colorectal cancers almost always arise from initially benign colon polyps that must be removed in good time before they become carcinogenic. Of recent years, virtual colonography has been developed as a non-invasive method for diagnosing colon polyps as an alternative to colonoscopy. The procedure is based on a visualization of a 3D image data record, obtained by way of computed tomography, of the abdominal region of a patient. In advance of the investigation, it is customary to clean the colon and to mark stool remainders with the aid of a contrast medium. During the investigation, carbon dioxide is introduced into the colon through a small catheter in order to enable a better reconstruction of the intestinal walls.

A number of methods are applied nowadays to visualize the data. One of these methods comprises the so-called fly-through visualization mode, in the case of which a virtual camera that serves the purpose of 3D utilization is moved along the closed colon in a manner similar to a colonoscopy. In accordance with an alternative method, the so-called colon-flattening method, the inner walls of the colon are displayed as a plane. The disadvantage of this method is, however, that it requires complicated pre-processing steps and is therefore computationally complicated. In addition, the colon walls are distorted by their display in a plane, and so it becomes difficult to detect small of flat polyps. A combined method is described in US 2008/0055308 A1. A virtual camera is moved along the centerline of a colon, and the inner walls of the colon can be displayed both in a perspective image and in a developed, flat image.

SUMMARY

In at least one embodiment of the invention, a visualization of an endo-image data record of an organ enclosing a cavity is specified, in particular a CT image data record of a colon, that is reliable and has a low level of computational complexity.

According to at least one embodiment of the invention, a method is disclosed for visualizing an image data record of an organ enclosing a cavity, in particular a CT image data record of a colon, in the case of which a virtual viewer position outside the organ tissue is defined, an interface between the organ tissue and the cavity is determined with the aid of the image data record, from the middle of the cavity local gradients that specify the rise in the absorption behavior between a gas contained in the cavity and with the organ tissue are determined, starting from the viewer position, a search beam is defined and an angle between the search beam and the gradients a is determined, a transparency value is allocated to the organ tissue as a function of the angle during visualization, and, a side of the organ facing the viewer position is displayed at least partially transparently, in particular for an angle <90°, in order to enable a view onto an inner wall of the side of the organ averted from the viewer position.

According to at least one embodiment of the invention an apparatus is disclosed for carrying out the method.

It is decisive for the detection of the polyps that a good and, as far as possible, uncovered view onto the colon inner wall be ensured. In order to enable this, at least one embodiment of the invention offers a completely new concept, in terms of which the colon inner walls are displayed in their original shape and it is possible to investigate them by showing, partially or completely transparently, tissue of the colon that covers the view from the viewer position.

In a first step, there is defined in this case the virtual viewer position that is located outside the displayed organ tissue with regard to a simpler evaluation of the image data record.

In a further step, the interface between the organ tissue, here the colon tissue, and a gas contained in the cavity, in this case carbon dioxide, is determined. In the case of the algorithm for evaluating the image data, it is provided to calculate in all three spatial directions the simple intensity gradients that specify the difference in the absorption behavior of the gas contained in the cavity, and of the organ tissue. Since the gas has a much lower density than the tissue, and correspondingly absorbs a much smaller proportion of the X-rays during the CT scan, these gradients always point outward.

Subsequently, a virtual search beam that specifies the viewing direction and cuts the organ tissue is defined from the viewer position. In this process, the angles between the search beam and the previously determined gradients are determined in stepwise fashion. For tissue regions that lie on the side of the colon facing the viewer position, the gradients enclose an angle with the search beam of <90°. A corresponding statement holds for the side of the colon averted from the viewer position, namely that the angles between the gradients and the search beam in this region are >90°.

This information can be used to determine which pixels of the computerized display of the colon lie on the side of the viewer position in the viewing direction, and which do not. Correspondingly, the regions of the colon which cover the view from the viewer position can be masked out such that only the inner wall, lying therebehind, of the colon is indicated. In this case, a side of the organ facing the viewer position is displayed at least partially transparently, in particular for an angle <90°, in order to enable the view onto an inner wall of the side of the organ averted from the viewer position.

In order to obtain a display only of the inner colon wall, in which display, for example, the boundary between the skin surface and the air is excluded, when determining the interface a pre-selection of the region to be displayed is preferably made by generating a binary mask of the organ tissue at the interface. The generation of the binary mask is performed in the context of a pre-processing step, in particular by an explicit segmentation of the data records, in the case of which the value 0 is allocated to the carbon dioxide in the colon, and the value 1 is allocated to the organ tissue. This determines a particularly clear boundary between the cavity and the organ tissue that is applied to mask the region to be displayed.

According to at least one further example embodiment, the mask specifying the organ is expanded by an empirical value for the thickness of the organ tissue. This means that not only is the interface between the cavity and the organ tissue output, but that the region in the data record that corresponds to the colon is covered by the binary mask. This is done in order to ensure that the entire colon wall is displayed. Moreover, thanks to the mask it is only the organ to be investigated that is selected from the voluminous data record and visualized, the result being a clear reduction in the computational outlay and computing time.

According to at least one further example embodiment, the mask is stored as a data subset. Consequently, a second data record, which is stored separately from the original data record, is obtained after the pre-processing step, the result being that no information is lost and that the original data record can continue to be used for re-evaluation and visualization.

An implicit segmentation of the image data record is preferably carried out when displaying the organ inside the preselected region. During image processing, the volume data record is generally split by the segmentation into a plurality of regions that are homogeneous with reference to their properties, such as, for example, with reference to their density or absorption behavior. On the basis of the implicit segmentation there is the assumption that one or more features for each element of the data record can be calculated from the data record, and that these features belong to a specific exclusive class. The different materials or types of tissue can also be displayed differently thereby in the visualization. Consequently, in the implicit segmentation "homogeneous" regions of the volume data record are displayed uniformly in the visualization. However, the implicit segmentation alone does not suffice in being able to distinguish the side of the colon facing the viewer from that averted from the viewer. For this reason, the implicit segmentation in accordance with the described method is supplemented by the determination of the local gradients.

A direct volume rendering (DVR) technique is advantageously applied in the implicit segmentation. In medicine, particularly during the visualization of 3D volume records that are obtained by computed tomography, for example, indirect three-dimensional methods such as the surface rendering technique, for example, frequently supply an inadequate quality of the display. In order to improve the quality, the DVR technique, in which the information for image display is taken directly from the original 3D data record, is therefore used in this case. According to a preferred variant, the transparency value can be set. The transparency value can, in particular, have analog values between 0 for a complete opacity and 1 for a complete transparency. These values are, in particular, defined by the user and can be changed manually at any time during the visualization. Moreover, a user can assign different transparency values to the different regions of the colon.

In order to enable the entire inner wall of the colon to be investigated without any problem, according to a further preferred variant the viewer position can be varied during the visualization. Here, the colon can be viewed from different sides and angular positions, the result being that another site of the inner wall is always visible. The viewer position can, in particular, be defined and changed by the user. It is possible, in particular, with the present method to move the virtual camera in both directions along the colon such that it describes a circle around the colon, it thereby being possible to cover the entire inner surface of the colon.

In order to determine a 3D impression that greatly facilitates the diagnosis, a conditioning of an image produced with the aid of the data record is advantageously carried out. In this case, the different materials and tissues as well as regions of the colon are, for example, allocated various colors, illumination and shading that ensure a display which is as realistic as possible.

BRIEF DESCRIPTION OF THE DRAWINGS

An example embodiment of the invention is explained in more detail with the aid of the drawings, in which.

Identically acting parts are provided in the figures with identical reference symbols.

DETAILED DESCRIPTION OF THE EXAMPLE EMBODIMENTS

Figure 1:
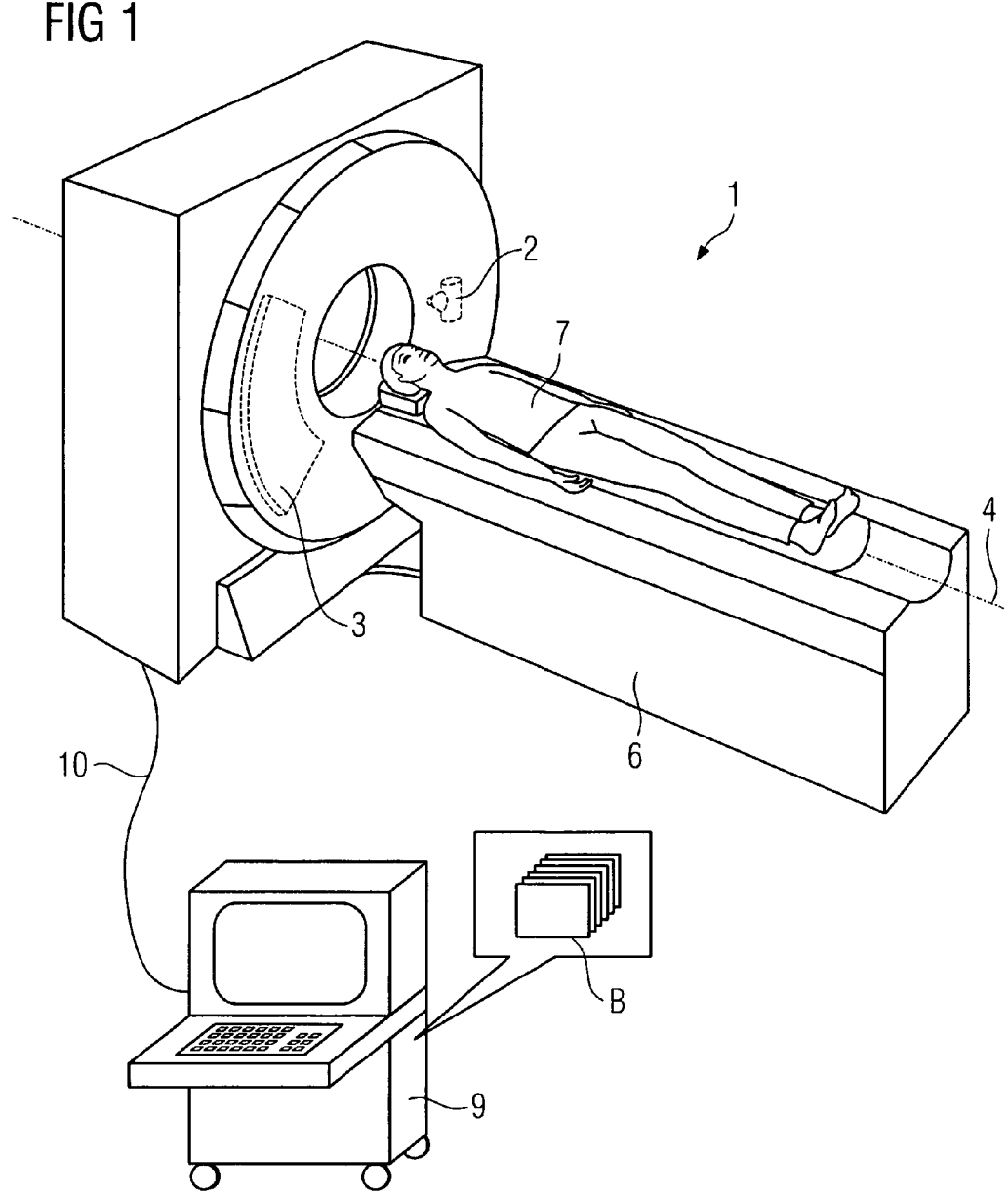
FIG. 1 shows a schematic of a computed tomography system for producing an image data record.
Figure 2:
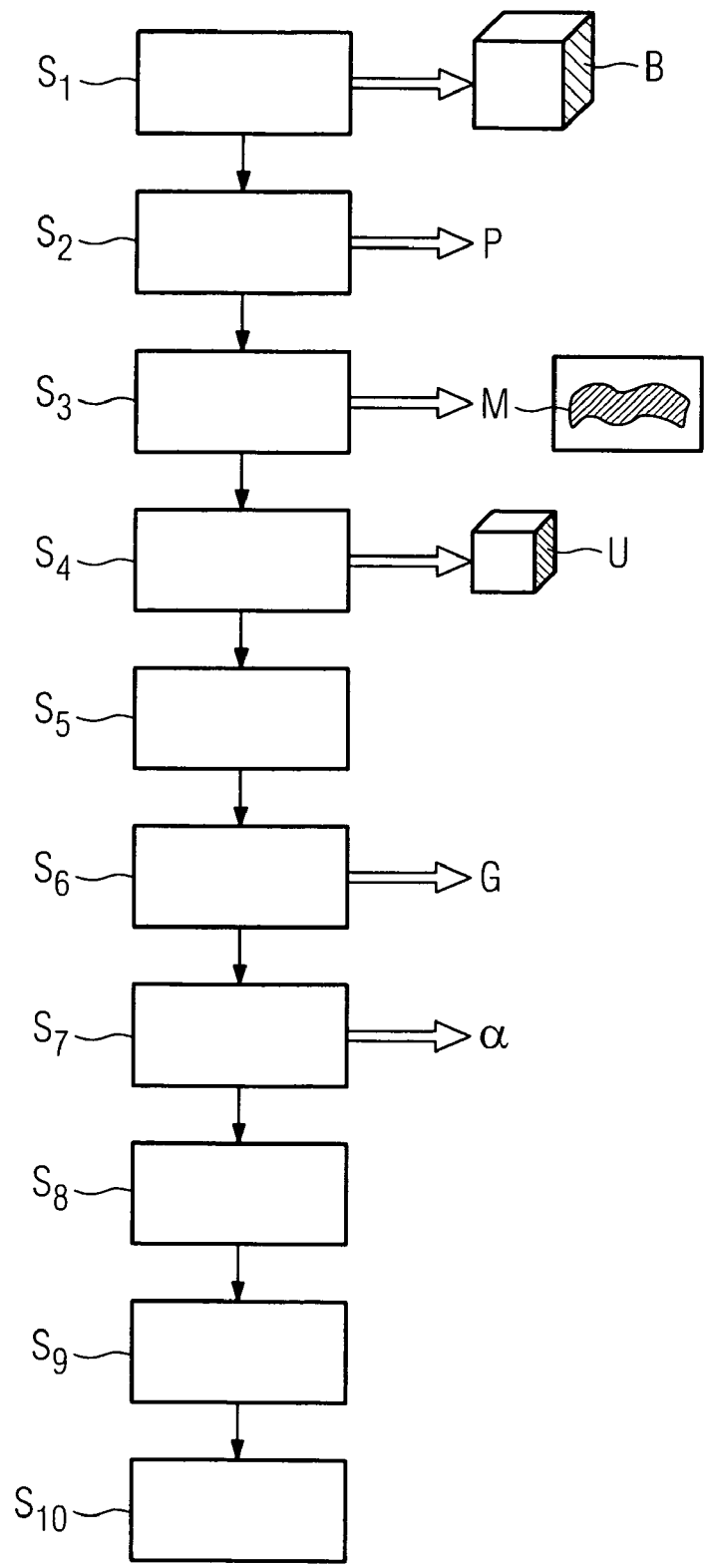
FIG. 2 shows a block diagram of the method steps for visualizing the image data record.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a computed tomography system 1 with the aid of which an image data record B of the abdominal region of a patient 7 is obtained. The image data record B serves for investigating the colon C (see FIG. 3) of the patient 7. Carbon dioxide is introduced into the colon for the purpose of improved imaging.

The computed tomography system 1 comprises a gantry with a circularly revolving X-ray tube 2 and a detector 3 situated opposite. The patient 7 is positioned on a patient couch 6 in order for the purpose of the scanning operation to be moved into the opening of the computed tomography system 1. During the scanning operation, in which the X-ray tube 2 moves in a circle around the patient 7, a relative movement of the patient in the direction of a system axis 4 takes place. In this process, a spiral scanning can be performed relative to the patient 7, or the patient 7 can also be scanned by being pushed sequentially forward during a scanning pause in many circular movements of the tubes 2.

The computed tomography system 1 is controlled by an arithmetic logic unit 9 via a control data line 10. Moreover, the data collected by the detector 3 are transmitted to the computer 9 via the control data line 10. The arithmetic logic unit 9 has internal memories and arithmetic processors via which a plurality of programs for controlling the computed tomography system 1 and for evaluating the data record B obtained during the scanning operation are executed.

With the aid of the computed tomography system 1, the image data record B, which contains information relating to the colon of the patient 7, is obtained in a first step S1. Next, the viewer position P (see FIG. 3) outside the colon tissue is defined in step $S_2$. In the pre-processing step $S_3$ following thereupon, an explicit segmentation of the carbon dioxide in the colon is carried out in order to determine the interface between the colon tissue and the carbon dioxide contained in the colon. The binary mask M resulting therefrom, which specifies the colon tissue, is additionally expanded by a known value for the thickness of the colon in order to ensure that the colon tissue surrounding the interface is incorporated into the mask M. This procedure produces a data subset U that includes information relating only to the colon tissue, and is stored in step $S_4$ separately from the original image data record B.

After the binary masking of the original volume data record B, an implicit segmentation of the colon wall is performed in step $S_5$; it is accomplished in a known way by applying a transfer function for visualizing the boundary between the carbon dioxide and the tissue. The implicit segmentation is performed here by means of the DVR technique without the need for complicated pre-processing steps.

Figure 3:
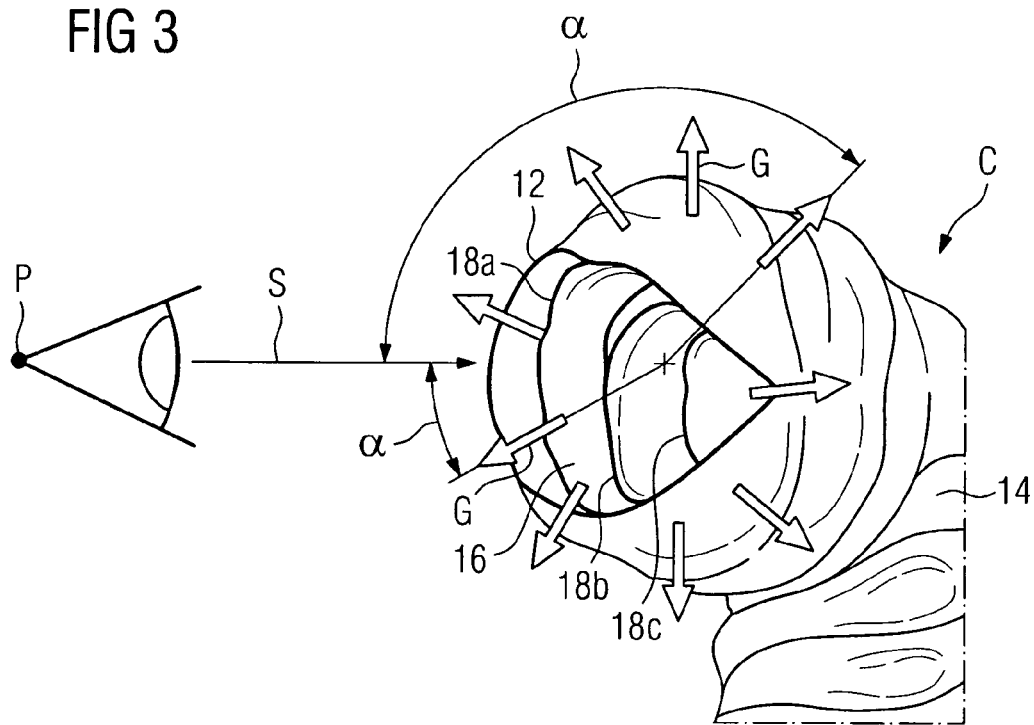
FIG. 3 shows a cross section through a colon with an indicated viewer position outside the colon.

However, there is still no possible direct view onto the inner surface of the colon after the implicit segmentation, since the segmentation with the transfer function is not sufficient for a viewer in the viewer position P, which is specified schematically in FIG. 3 by an eye, to be able to distinguish between the facing side and the averted side of the colon C. Against this background, in step $S_6$ a calculation is made for each pixel that displays the colon wall as to whether the pixel is located on the side of the colon C facing, or averted from, the viewer. To this end, the local gradients or intensity gradients G that specify the rise in the density or the absorption behavior at the boundary between the carbon dioxide and the colon tissue are determined. Since the colon is filled with carbon dioxide, and the colon tissue has a greater absorption behavior than the gas, the gradients G always point outward, as is shown in FIG. 3.

In the cut through the colon C in accordance with FIG. 3, the front, closed ring specifies the boundary line 12 between the outside 14 of the colon and the inside 16 of the colon, or its inner wall. The tissue visible inside the boundary line 12, which extends rearward as seen from the plane of the drawing, has a plurality of dark lines that display the folds 18a, 18b, 18c of the inner wall 16. In a way similar to the inside 16, the outer wall 14 of the colon C has a strongly corrugated surface with many folds. The viewer position P is defined on the side of the colon C such that the viewing angle differs by 90° from the viewing direction in accordance with FIG. 3, as seen from the viewer position P.

Subsequently, during evaluation of the image data record B a search beam S that cuts the colon tissue C is defined from the viewer position B in the viewing direction onto the colon C. In step $S_7$, for each pixel on the outer wall 14 of the colon C, the angle α between the search beam S shown and the local gradient G is then determined by this pixel. For the search beam S, the angle α is smaller than 90° for points on the surface of the colon C that cover the view onto the inner wall 16 of the colon C. In a similar way, the angle α for points on the side of the colon C averted from the viewer is greater than 90°.

When the respective angle α is known, a transparency value is allocated in step $S_8$ to the regions of the colon C that cover the view onto the inner wall 16. In particular, pixels with an angle α<90° are allocated a transparency value of 1 such that these can be completely masked out and a free view onto the inner wall 16 of the side of the colon C facing the viewer at the point P is produced. The transparency value varies here between 0 for a completely opaque tissue and 1 for a completely transparent tissue, it being possible to set the transparency or opacity of the tissue by a user. For example, the transparency value can be selected as a function of the absolute value of the angle.

During the image processing, different colors, intensity, illumination and shading are, moreover, allocated to the individual pixels in step $S_9$. Consequently, a 3D impression, in particular, is conveyed in the display of the colon C.

The visualization of the colon C is performed in the last method step $S_{10}$. The described method enables a quick and accurately detailed visualization of the inner wall 16 of the colon C with a high image quality. Whereas the DVR technique enables only a display of the outer wall 14 of the colon C, after the masking out of parts of the colon C it is possible to investigate the inner wall 16 from different viewer positions. Irrespective of the viewer position, the inner wall 16 of the colon C can always be seen, and pathologies can be uncovered by rotating the viewer position P around the colon C. In the investigation, the colon C can in this case be rotated about a number of axes and approached by zooming such that the exact viewing of individual, enlarged wall sections is simplified. Overall this method can be linked, as a first, global overview for the detection of polyps, with other investigation methods.

An embodiment of the present method has been explained with the aid of the visualization of an image data record of a colon. However, an embodiment of the method can be used to display the inner wall 16 of further, in particular tubular organs. The most important precondition for this is only that a gradient be formed between a medium, contained in the interior of the organ, and the organ tissue, with the aid of which the transparency values can be allocated such that only the inner wall 16 of the organ is shown.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing an image data record of an organ enclosing a cavity, the method comprising:
   defining a virtual viewer position outside the organ tissue;
   determining an interface between the organ tissue and the cavity, with the aid of the image data record;
   determining, from the middle of the cavity, local gradients that specify a rise in absorption behavior between a gas contained in the cavity and the organ tissue;
   defining, starting from a viewer position, a search beam and determining an angle between the defined search beam and the determined local gradients; and
   allocating a transparency value to the organ tissue as a function of the determined angle during visualization.

2. The method as claimed in claim 1, wherein a side of the organ facing the viewer position is displayed at least partially transparently in order to enable a view onto an inner wall of the side of the organ averted from the viewer position.

3. The method as claimed in claim 2, wherein, when determining the interface between the gas and the organ tissue, a pre-selection of the region to be displayed is made by generating a binary mask of the organ tissue at the interface.

4. The method as claimed in claim 3, wherein the mask specifying the organ is expanded by an empirical value for the thickness of the organ tissue.

5. The method as claimed in claim 4, wherein the mask is stored as a data subset.

6. The method as claimed in claim 3, wherein an implicit segmentation of the image data record is carried out when displaying the organ inside the pre-selected region.

7. The method as claimed in claim 6, wherein a direct volume rendering technique is applied in the implicit segmentation.

8. The method as claimed in claim 1, wherein the transparency value is settable.

9. The method as claimed in claim 1, wherein the viewer position is variable during the visualization.

10. The method as claimed in claim 1, wherein a conditioning of an image produced, with the aid of the image data record, is carried out.

11. An apparatus for carrying out the method as claimed in claim 1.

12. The method as claimed in claim 1, wherein the method for visualizing a CT image data record of a colon.

13. The method as claimed in claim 1, wherein a side of the organ facing the viewer position is displayed at least partially transparently, for an angle (.alpha.)<90.degree., in order to enable a view onto an inner wall (of the side of the organ averted from the viewer position.

14. The method as claimed in claim 1, wherein, when determining the interface between the gas and the organ tissue, a pre-selection of the region to be displayed is made by generating a binary mask of the organ tissue at the interface.

15. A computer readable medium including program segments for, when executed on a computer device, causing the computer device to implement the method of claim 1.

16. An apparatus for visualizing an image data record of an organ enclosing a cavity, the apparatus comprising:

means for defining a virtual viewer position outside the organ tissue;

means for determining an interface between the organ tissue and the cavity, with the aid of the image data record;

means for determining, from the middle of the cavity, local gradients that specify a rise in absorption behavior between a gas contained in the cavity and the organ tissue;

means for defining, starting from a viewer position, a search beam and determining an angle between the defined search beam and the determined local gradients; and means for allocating a transparency value to the organ tissue as a function of the angle during visualization.

17. The apparatus as claimed in claim 16, further comprising:

means for displaying a side of the organ facing the viewer position, at least partially transparently, in order to enable a view onto an inner wall of the side of the organ averted from the viewer position.

18. A method for visualizing an image data record of an organ enclosing a cavity, the method comprising:

defining a virtual viewer position outside the organ tissue;

determining an interface between the organ tissue and the cavity, with the aid of the image data record;

determining, from the middle of the cavity, local gradients that specify a rise in absorption behavior between a gas contained in the cavity and the organ tissue;

defining, starting from a viewer position, a search beam and determining an angle between the defined search beam and the determined local gradients; and visualizing the image data record of the organ enclosing the cavity, wherein a transparency value is allocated to the organ tissue as a function of the determined angle during visualization.

19. The method as claimed in claim 18, wherein a side of the organ facing the viewer position is displayed at least partially transparently in order to enable a view onto an inner wall of the side of the organ averted from the viewer position.

20. A computer readable medium including program segments for, when executed on a computer device, causing the computer device to implement the method of claim 18.

* * * * *